US010526259B2

(12) United States Patent
Senetar et al.

(10) Patent No.: US 10,526,259 B2
(45) Date of Patent: Jan. 7, 2020

(54) STAGED PRESSURE FOR BUTADIENE REACTORS TO ENHANCE ENERGY RECOVERY

(71) Applicants: UOP LLC, Des Plaines, IL (US); TPC Group LLC, Houston, TX (US)

(72) Inventors: John J. Senetar, Des Plaines, IL (US); Jillian M. Horn, Decatur, GA (US)

(73) Assignees: UOP LLC, Des Plaines, IL (US); TPC Group LLC, Houston, TX (US)

( * ) Notice: Subject to any disclaimer, the term of this patent is extended or adjusted under 35 U.S.C. 154(b) by 0 days.

(21) Appl. No.: 15/755,810

(22) PCT Filed: Aug. 25, 2016

(86) PCT No.: PCT/US2016/048529
§ 371 (c)(1),
(2) Date: Feb. 27, 2018

(87) PCT Pub. No.: WO2017/040165
PCT Pub. Date: Mar. 9, 2017

(65) Prior Publication Data
US 2018/0327337 A1 Nov. 15, 2018

Related U.S. Application Data

(60) Provisional application No. 62/211,781, filed on Aug. 29, 2015.

(51) Int. Cl.
*C07C 5/48* (2006.01)
(52) U.S. Cl.
CPC .......... *C07C 5/48* (2013.01); *C07C 2523/02* (2013.01); *C07C 2523/22* (2013.01);
(Continued)

(58) Field of Classification Search
CPC ........................................... C07C 5/48
See application file for complete search history.

(56) References Cited

U.S. PATENT DOCUMENTS 3,067,272 A * 12/1962 Voge ................ B01J 23/28
502/208
5,489,724 A 2/1996 Harandi
(Continued)

FOREIGN PATENT DOCUMENTS

CN 102675027 A 9/2012
CN 103071544 A 5/2013
(Continued)

OTHER PUBLICATIONS

Machine translation CN103965004. Aug. 6, 2014 (Year: 2014).*
(Continued)

*Primary Examiner* — Philip Y Louie
*Assistant Examiner* — Alyssa L Cepluch
(74) *Attorney, Agent, or Firm* — Greer, Burns & Crain, Ltd.

(57) ABSTRACT

A process is presented for the oxidative dehydrogenation of butenes to butadienes. The process includes the use of parallel reactors, wherein the reactors are operated at different pressures. A butene feedstream is split into several portions wherein each portion is passed to a different reactor. Each reactor generates an effluent stream, and the effluent stream is cooled to generate steam for use in a lower pressure reactor.

20 Claims, 1 Drawing Sheet

(52) U.S. Cl.
CPC ...... *C07C 2523/26* (2013.01); *C07C 2523/28* (2013.01); *C07C 2523/745* (2013.01); *C07C 2523/80* (2013.01); *Y02P 20/51* (2015.11)

(56) References Cited

U.S. PATENT DOCUMENTS

| | | | |
|---|---|---|---|
| 2011/0034330 A1* | 2/2011 | Czaja | ..................... B01J 23/002 502/243 |
| 2011/0245568 A1 | 10/2011 | Khabashesku et al. | |
| 2013/0281748 A1* | 10/2013 | Cha | ........................... B01J 8/04 585/302 |
| 2014/0088331 A1 | 3/2014 | Rolland | |
| 2014/0100405 A1 | 4/2014 | Brummer et al. | |
| 2014/0221719 A1 | 8/2014 | Yang et al. | |

FOREIGN PATENT DOCUMENTS

| | | | |
|---|---|---|---|
| CN | 103073382 A | | 5/2013 |
| CN | 103304359 A | * | 9/2013 |
| CN | 103553864 A | | 2/2014 |
| CN | 103965004 A | * | 8/2014 |

OTHER PUBLICATIONS

Machine translation CN103304359. Sep. 18, 2013 (Year: 2013).*
International Search Report for International Application No. PCT/US2016/048529, dated Dec. 8, 2016, 2 pages.

* cited by examiner

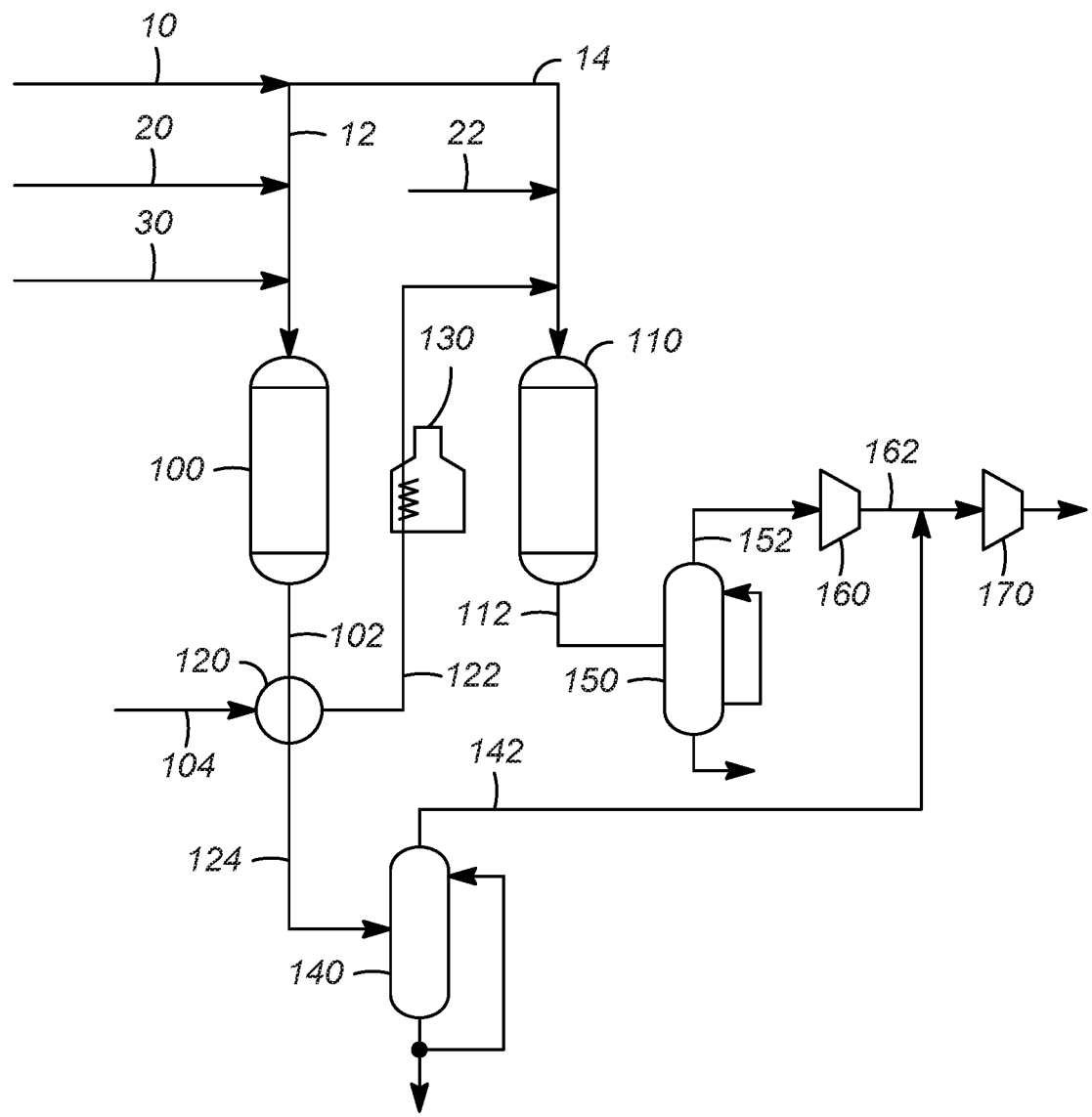

STAGED PRESSURE FOR BUTADIENE REACTORS TO ENHANCE ENERGY RECOVERY

STATEMENT OF PRIORITY

This application is a U.S. National Phase under 35 U.S.C. § 371 of International Application No. PCT/US2016/048529, filed Aug. 25, 2016, which claims priority to U.S. Application No. 62/211,781 which was filed Aug. 29, 2015, the contents of which are hereby incorporated by reference in their entirety.

FIELD OF THE INVENTION

The present invention relates to a process for the production of butadiene. The process involves butadiene production through multiple reactors with successively reduced pressures.

BACKGROUND OF THE INVENTION

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers are light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

Another important monomer is butadiene. Butadiene is a basic chemical component for the production of a range of synthetic rubbers and polymers, as well as the production of precursor chemicals for the production of other polymers. Examples include homopolymerized products such as polybutadiene rubber (PBR), or copolymerized butadiene with other monomers, such as styrene and acrylonitrile. Butadiene is also used in the production of resins such as acrylonitrile butadiene styrene.

Butadiene is typically recovered as a byproduct from the cracking process, wherein the cracking process produces light olefins such as ethylene and propylene. With the increase in demand for rubbers and polymers having the desired properties of these rubbers, an aim to improving butadiene yields from materials in a petrochemical plant will improve the plant economics.

SUMMARY OF THE INVENTION

The present invention is a process for improving the energy efficiency in the production of 1,3 butadiene. The process utilizes parallel reactors operated at different pressures.

A first embodiment of the invention is a process for the production of 1,3 butadiene, comprising splitting a feedstream comprising butene into two portions; passing an oxidizing agent and steam to a first reactor; passing a first portion of the feedstream to the first reactor operated at first reaction conditions to generate a first reactor effluent; passing water through a heat exchanger to cool the first reactor effluent and generate a low pressure steam stream and a cooled first reactor effluent; passing an oxidizing agent and the low pressure steam stream to a second reactor; and passing a second portion of the feedstream to the second reactor operated at second reaction conditions to generate a second reactor effluent. An embodiment of the invention is one, any or all of prior embodiments in this paragraph up through the first embodiment in this paragraph further comprising passing the cooled first reactor effluent to a quench tower to generate a quenched first reactor effluent. An embodiment of the invention is one, any or all of prior embodiments in this paragraph up through the first embodiment in this paragraph further comprising passing the second reactor effluent to a second quench tower to generate a quenched second reactor effluent. An embodiment of the invention is one, any or all of prior embodiments in this paragraph up through the first embodiment in this paragraph wherein the first reaction conditions include a pressure 300 kPa to 800 kPa. An embodiment of the invention is one, any or all of prior embodiments in this paragraph up through the first embodiment in this paragraph wherein the second reaction conditions include a pressure 100 kPa to 300 kPa. An embodiment of the invention is one, any or all of prior embodiments in this paragraph up through the first embodiment in this paragraph wherein the oxidizing agent is air. An embodiment of the invention is one, any or all of prior embodiments in this paragraph up through the first embodiment in this paragraph wherein the steam to butene ratio in the feed to the first reactor is greater than 9 to 1. An embodiment of the invention is one, any or all of prior embodiments in this paragraph up through the first embodiment in this paragraph wherein the steam to butene ratio in the feed to the second reactor is between 1 to 1 and 5 to 1. An embodiment of the invention is one, any or all of prior embodiments in this paragraph up through the first embodiment in this paragraph wherein the first reaction conditions includes a catalyst on a support. An embodiment of the invention is one, any or all of prior embodiments in this paragraph up through the first embodiment in this paragraph wherein the catalyst is selected from the group consisting of zinc ferrite, vanadium oxide, molybdenum oxide, chromium oxide, vanadium-magnesium oxide catalyst, and a combination of the metal oxides. An embodiment of the invention is one, any or all of prior embodiments in this paragraph up through the first embodiment in this paragraph wherein the support is selected from the group consisting of aluminas, zirconia, titania, magnesia, refractory materials, and mixtures thereof.

A second embodiment of the invention is a process for the oxidative dehydrogenation of a butene feedstock, comprising splitting the butene feedstock into a plurality of portions, wherein each portion is passed to a separate reactor in a plurality of parallel reactor, and wherein the reactors are operated at different pressures, and wherein the reactors operating in parallel have decreasing pressures with the first reactor having the highest pressure and the last reactor having the lowest pressure; passing an oxidizing agent to each reactor; passing steam to each reactor, wherein the steam is passed in a decreasing amount and pressure to each reactor operated at a lower pressure to generate an effluent stream from each reactor; and passing each reactor effluent to a quench tower to generate a cooled process stream with a reduced water content. An embodiment of the invention is one, any or all of prior embodiments in this paragraph up through the second embodiment in this paragraph wherein the plurality of reactors is between 2 and 6 reactors. An embodiment of the invention is one, any or all of prior embodiments in this paragraph up through the second embodiment in this paragraph further comprising passing each cooled process stream to a compressor to generate a compressed product stream. An embodiment of the invention is one, any or all of prior embodiments in this paragraph up through the second embodiment in this paragraph wherein the pressures in the reactors are in decreasing values from 1000 kPa to 100 kPa. An embodiment of the invention is one, any or all of prior embodiments in this paragraph up through the second embodiment in this paragraph wherein the steam to butene ratios are in decreasing values from 9 to 1 to 1 to 1. An embodiment of the invention is one, any or all of prior embodiments in this paragraph up through the second embodiment in this paragraph wherein the steam used in each reactor after the first reactor is partially generated by cooling the first reactor effluent stream. An embodiment of the invention is one, any or all of prior embodiments in this paragraph up through the second embodiment in this paragraph wherein the ratio of steam to butene decreases from the first reactor to the last reactor. An embodiment of the invention is one, any or all of prior embodiments in this paragraph up through the second embodiment in this paragraph further comprising passing the cooled process stream to a compressor to generate a compressed product stream. An embodiment of the invention is one, any or all of prior embodiments in this paragraph up through the second embodiment in this paragraph further comprising passing the compressed product stream to a butadiene recovery unit.

Other objects, advantages and applications of the present invention will become apparent to those skilled in the art from the following detailed description and drawings.

BRIEF DESCRIPTION OF THE DRAWING

FIGURE is a diagram of the process and staged reactors for a two reactor system.

DETAILED DESCRIPTION OF THE INVENTION

The production of butadiene is commonly done with the oxidative dehydrogenation of butene to butadiene. The process is highly exothermic and requires a means for absorbing the heat released in order to carry out the process economically. The common process is to add steam to the reaction mixture. The steam acts as a heat sink and also acts to keep the reaction mixture outside of the flammability envelop. In order to perform these functions, a large amount of steam is added.

The capital and operating costs associated with steam production greatly impact the economics for the process. Ideally one would like to recover the heat of condensation of the steam in the reactor effluent to generate additional steam. Such an option is not possible using a conventional approach, as the temperature required to generate steam fed to the reactor is higher than the condensation temperature of the reactor effluent (the effluent being at lower pressure than the feed and also being not pure steam). One can circumvent this situation by vaporizing the steam at a lower pressure and compressing it, or alternatively compressing the reactor effluent so that it condenses at a higher pressure. Either way, a large compressor is required.

The present invention reduces the utilities required for steam generation without the need of an additional compression step. The invention operates two or more oxidative dehydrogenation reactors in parallel, with a reduction in pressure from one reactor to the next. In particular, a two or three reactor system is envisioned, but more can also be used.

For a two reactor system, there is a high pressure reactor and a low pressure reactor, as shown in the FIGURE. The process for the production of 1,3 butadiene includes splitting a butene feed 10 into two portions, a first portion 12 and a second portion 14. An oxidizing agent 20 is and high pressure steam 30 is passed to a first reactor 100, with the first portion 12, to generate a first reactor 100 effluent 102. The first reactor effluent 102 is passed through a heat exchanger 120 to heat a water stream 104 that is passed to the heat exchanger 120 to generate a low pressure steam 122, and a cooled first reactor effluent 124. The second portion 14 is passed to the second reactor 110. An oxidizing agent 22 and the low pressure steam 122 is passed to the second reactor 110 to generate a second reactor effluent 112.

The low pressure stream 122 can be passed through a steam superheater 130 to raise the temperature of the low pressure steam 122 before passing the low pressure steam to the second reactor 110.

The process can further include passing the cooled first reactor effluent 124 to a quench tower 140 to further cool and to remove most of the water from the effluent stream to generate a first quenched effluent stream 142. The process can also include passing the second reactor effluent 112 to a second quench tower 150 to generate a second quenched effluent stream 152.

The reaction conditions of the first reactor include a pressure between 300 kPa and 800 kPa, and the reaction conditions in the second reactor include a pressure between 100 kPa and 300 kPa. The preferred oxidizing agent is air, but other oxidizing agents can be used based upon availability. The feed temperatures for the reactors are from 300° C. to 1000° C. at the inlet. Preferably, the inlet temperature of the reactor is from 300° C. to 450° C., while the temperature in the reactor can rise substantially, to 1000° C. or more. The temperature at the inlet can depend on the catalyst selected, and the pressure of the reactor. In order to moderate the temperature rise, steam is added to the feed at the reactor inlet.

The quenched effluent streams 142 and 152 can be passed to compressors to generate a compressed product stream. In this invention, the second quenched effluent stream 152 is passed to a first compressor unit 160 to bring the second quenched effluent stream pressure up to the pressure of the first quenched effluent stream 142. The compressed second quenched effluent stream 162 is combined with the first quenched effluent stream 142, and the combined streams are passed to a second compressor 170.

The process conditions for the first reactor include sufficient stream such that the steam to butene molar ratio in the feed to the first reactor is greater than 9 to 1. The process conditions for the second reactor include a steam to butene molar ratio in the feed to the second reactor is between 1 to 1 and 5 to 1.

The reactors include a catalyst for the butene oxidative dehydrogenation process. Catalysts useful in oxidative dehydrogenation of butene include zinc ferrite, vanadium oxide, molybdenum oxide, chromium oxide, vanadium-magnesium oxide catalyst, or a combination of these metal oxides. The catalyst is deposited on a support, wherein support materials for the catalyst include refractory materials, aluminas, zirconia, titania, magnesia and mixtures of these support materials.

In another embodiment, it is envisioned that the invention encompasses a plurality of reactors operated in parallel, where a first reactor is operated at a high pressure, and subsequent neighboring reactors are operated at successively lower pressures. The plurality of reactors is preferably between 2 and 6 reactors. The reactors are operated at pressures between 100 kPa (absolute) and 1000 kPa (absolute), with the first reactor operated at the highest pressure, and each subsequent parallel reactor operated at a lower pressure.

The process includes splitting the butene feedstock into a plurality of portions, wherein each portion is passed to a separate reactor in a plurality of reactors operated in parallel. An oxidizing agent is passed to each reactor. A steam stream is passed to each reactor, and each reactor generates an effluent stream comprising butadienes.

Each reactor, in order of decreasing pressure, receives steam in order of decreasing pressure. The steam generated for the lower pressure reactors is generated by cooling the effluent stream with water to generate lower pressure steam, from the effluent stream of a reactor operated at higher pressure. The lower pressure steam is passed to a steam superheater to raise the temperature of the steam, before passing the steam to a lower pressure reactor.

Each effluent stream, after passing through a heat exchanger to cool the effluent stream and generate a lower pressure steam, is passed to a quench tower. The effluent stream is quenched to reduce the water content in the effluent stream, generating a cooled and quenched effluent stream. Each cooled and quenched effluent stream can be passed to a compressor to generate a compressed product stream. Since each effluent stream is at a different pressure, each stream can be compressed to the level of the next lowest pressure stream and combined with the combined stream compressed to the next pressure level, until all the effluent streams are compressed to a product delivery pressure.

The feed to each reactor comprises steam, butene, and an oxidizing agent. The steam to butene molar ratio can be in decreasing values as one progresses from the highest pressure reactor to the lowest pressure reactor. The stream to butene ratio in the feed to the highest pressure reactor can be 9:1 or greater, with the ratio of stream to butene decreasing to as low as 1:1 for the lowest pressure reactor.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for the production of 1,3 butadiene, comprising:
    splitting a feedstream comprising butene into two portions;
    passing an oxidizing agent and a first steam stream to a first reactor;
    passing a first portion of the feedstream to the first reactor operated at first reaction conditions including a first pressure to generate a first reactor effluent;
    passing water and the first reactor effluent through a heat exchanger to generate a second steam stream having a pressure less than the first stream and a cooled first reactor effluent;
    passing an oxidizing agent and the second steam stream to a second reactor; and
    passing a second portion of the feedstream to the second reactor operated at second reaction conditions including a second pressure less than the first pressure to generate a second reactor effluent.

2. The process of claim 1 further comprising passing the cooled first reactor effluent to a quench tower to generate a quenched first reactor effluent.

3. The process of claim 1 further comprising passing the second reactor effluent to a second quench tower to generate a quenched second reactor effluent.

4. The process of claim 1 wherein the first pressure is in a range of 300 kPa to 800 kPa.

5. The process of claim 1 wherein the second pressure is in a range of 100 kPa to 300 kPa.

6. The process of claim 1 wherein the oxidizing agent is air.

7. The process of claim 1 wherein a steam to butene ratio in the first reactor is greater than 9:1.

8. The process of claim 1 wherein a steam to butene ratio in the second reactor is between 1:1 and 5:1.

9. The process of claim 1 wherein the first reaction conditions include a catalyst on a support.

10. The process of claim 9 wherein the catalyst is selected from the group consisting of zinc ferrite, vanadium oxide, molybdenum oxide, chromium oxide, vanadium-magnesium oxide catalyst, and a combination of the metal oxides.

11. The process of claim 9 wherein the support is selected from the group consisting of zirconia, titania, refractory materials, and mixtures thereof.

12. A process for the oxidative dehydrogenation of a butene feedstock, comprising:
    splitting the butene feedstock into a plurality of portions, wherein each portion is passed to a separate reactor in a plurality of reactors, and wherein the reactors are operated at different pressures, and wherein the reactors operating in parallel have decreasing pressures with a first reactor having the highest pressure and each subsequent reactor having a lower pressure than a previous reactor;
    passing an oxidizing agent to each reactor;
    passing steam to each reactor, wherein the amount and pressure of steam passed to the first reactor being the highest and wherein the amount and pressure of steam passed to each subsequent reactor is less than the amount and pressure passed to the previous reactor to generate an effluent stream from each reactor; and
    passing each reactor effluent to a quench tower to generate a cooled process stream with a reduced water content compared to the reactor effluent prior to quenching.

13. The process of claim 12 wherein the plurality of reactors is between 2 and 6 reactors.

14. The process of claim 12 further comprising passing each cooled process stream to a compressor to generate a compressed product stream.

15. The process of claim 12 wherein the pressures in the reactors range from 1000 kPa to 100 kPa.

16. The process of claim 12 wherein a steam to butene ratio of the first reactor is greater than 9:1 and each subsequent reactor has a lower steam to butene ration that the previous reactor.

17. The process of claim 12 wherein the steam used in each reactor after the first reactor is partially generated by cooling the effluent stream from the first reactor.

18. The process of claim 17 wherein the ratio of steam to butene decreases from the first reactor to the last reactor.

19. The process of claim 12 further comprising passing the cooled process streams to a compressor to generate a compressed product stream.

20. The process of claim 19 further comprising passing the compressed product streams to a butadiene recovery unit.

* * * * *

UNITED STATES PATENT AND TRADEMARK OFFICE
CERTIFICATE OF CORRECTION

PATENT NO. : 10,526,259 B2
APPLICATION NO. : 15/755810
DATED : January 7, 2020
INVENTOR(S) : John J. Senetar and Jillian M. Horn Page 1 of 1

It is certified that error appears in the above-identified patent and that said Letters Patent is hereby corrected as shown below:

In the Claims

Column 6, Claim 1, Line 8, Insert the word --steam-- between the words "first" and "stream"

Column 6, Claim 12, Line 45, Insert the word --parallel-- between the words "of" and "reactors"

Signed and Sealed this
Twenty-sixth Day of May, 2020

Andrei Iancu
*Director of the United States Patent and Trademark Office*